United States Patent
Sekowski et al.

(10) Patent No.: US 7,629,129 B1
(45) Date of Patent: **\*Dec. 8, 2009**

(54) HAIR FOLLICLE BULB AS A BIODOSIMETER

(75) Inventors: Jennifer W. Sekowski, Forest Hill, MD (US); Amanda E. Chambers, Baltimore, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 129 days.

This patent is subject to a terminal disclaimer.

(21) Appl. No.: 11/416,509

(22) Filed: Apr. 26, 2006

Related U.S. Application Data (60) Provisional application No. 60/675,436, filed on Apr. 26, 2005, provisional application No. 60/740,294, filed on Nov. 15, 2005.

(51) Int. Cl.
*G01N 33/53* (2006.01)
(52) U.S. Cl. .......................... 435/7.1; 435/7.2; 436/518
(58) Field of Classification Search ................. 435/7.1, 435/7.2, 7.91, 7.92; 436/518
See application file for complete search history.

(56) References Cited

U.S. PATENT DOCUMENTS

| | | | | |
|---|---|---|---|---|
| 5,466,579 A | * | 11/1995 | Baumgartner | 435/7.1 |
| 5,688,765 A | * | 11/1997 | Sullivan | 514/12 |
| 6,395,562 B1 | * | 5/2002 | Hammock et al. | 436/518 |
| 2006/0105061 A1 | * | 5/2006 | Sha et al. | 424/728 |

OTHER PUBLICATIONS

Gundacker et al. Science Total Environment 2007, vol. 385, p. 37-47.*
Cheu et al. Carcinogenesis 1996 vol. 18, p. 167-175.*

* cited by examiner

*Primary Examiner*—Jacob Cheu
(74) *Attorney, Agent, or Firm*—Ulysses John Biffoni (57) ABSTRACT

The various embodiments provide method of using hair follicle bulbs as biodosimeters for the detection of chemical exposure. The methods described herein utilize intact, plucked hair follicle bulbs and can be used to monitor real-time or near real-time changes in the levels of specific follicular bulb biomarkers to determine exposure to toxicants. By utilizing the living, responsive cells in the plucked hair follicle bulb in an immunohistochemical (IHC) analysis, the various embodiments mitigate the risks of false positives associated with segmental hair analysis and avoid the more invasive collection required for serum and urinalysis.

8 Claims, 5 Drawing Sheets
(5 of 5 Drawing Sheet(s) Filed in Color)

HAIR FOLLICLE BULB AS A BIODOSIMETER

RELATED APPLICATIONS

This application claims priority to U.S. Provisional Patent Application Ser. No. 60/675,436, entitled "Hair Follicle as a Biodosimeter for Low-Level Exposure to OP Compounds," by Sekowski et al., and filed on Apr. 26, 2005; and U.S. Provisional Patent Application Ser. No. 60/740,294, entitled "Hair Follicle as a Biodosimeter for Exposure to Nitroaromatic and Cyclonitramine Explosive Compounds," by Sekowski et al., and filed on Nov. 15, 2005, which are commonly assigned and incorporated by reference herein in their entirety.

GOVERNMENTAL INTEREST

The invention described herein may be manufactured, used and licensed by or for the U.S. Government.

FIELD OF THE INVENTION

The present invention relates generally to immunohistochemistry, and in particular the present invention relates to the use of a hair follicle bulb as a biodosimeter for chemical exposure.

BACKGROUND

The skin covering the human body is rich in hair and hair follicles, with over 90% of its surface supporting some type of hair. Biologically defined, hair is the epidermal tissue that is derived from the involutions, called follicles, located in the skin. The bulb region of the hair follicle contains the metabolically active cells of the hair, which derive nutrients from the circulating blood. As such, hair follicle bulb cells are responsive in real-time or near real-time to toxic insults, in much the same way as skin cells.

Chemicals or heavy metals present in the body are brought into contact with the hair follicle by the circulating blood. There, they may enter the follicle and may potentially be incorporated into the hair shaft by the proliferating matrix cells found in the hair bulb. The ability to be incorporated into the hair shaft has led to the possibility of detecting exposure to chemicals and heavy metals via the hair shaft. Termed segmental hair analysis, this has become a popular method to determine exposure to drugs of abuse (e.g. cocaine, amphetamine, methamphetamine, heroin, marijuana, and steroids), therapeutic drugs (e.g. ephedrine, benzodiazepines, and barbiturates), and inorganic heavy metals (e.g. arsenic, lead, and mercury).

Recent reports suggest that long-term exposure to pesticides (e.g. carbamate, organochlorine, and organophosphate (OP)) can also be detected using segmental hair analysis. Others have demonstrated that methomyl, a carbamate pesticide, could be detected in the rabbit hair shaft following a 4-month daily methomyl exposure.

To carry out segmental hair analysis, scalp hair is cut into 1, 2, and 3 cm segments, which approximately corresponds to 1, 2, and 3 month's growth. If scalp hair is not available, other sources of hair can be used for analysis. Segmental analysis can be accomplished with as little as one hair or up to 200 mg of hair may be used to allow confirmation testing. The segments are typically washed to remove external contaminants and the chemicals in the hair are extracted by alkaline digestion, enzymatic treatment, or acid extraction. Several analytical methods are available to determine the concentration, if any, of a particular substance in the hair. Immunoassay, High Performance Liquid Chromatography (HPLC), Capillary Electrophoresis (CE), Gas Chromatography-Mass Spectrometry (GC-MS), tandem mass spectrometry (MS-MS) and Liquid Chromatography-Mass Spectrometry (LC-MS) can be used for analysis. Of these, the most superior in sensitivity, selectivity, and specificity is GC-MS separation and selective ion monitoring (SIM) quantitation. However, tandem MS can be used if the compound of interest is unstable in gas chromatograph separation/analysis.

The main advantage of segmental hair analysis is that successful analysis is possible even months after exposure. Other sample sources for testing, such as urine, offer an immediate window of testing, however, most drugs can only be detected 1 to 3 days following initial use. Although segmental hair analysis is becoming increasingly popular, the risk of a false positive is high when compared to urine or blood testing. Dark hair color, poor personal hygiene, and passive exposure can all lead to false positive segmental hair analysis results.

Due the increased risk of false positives associated with segmental hair analysis and the more invasive collection required for serum and urinalysis, and for other reasons stated below that will become apparent to those skilled in the art upon reading and understanding the present specification, there is a need in the art for alternative methods of determining levels of toxicant exposure.

SUMMARY

The various embodiments include the detection of chemical exposure through the preparation of intact, plucked hair follicle bulbs. The methods described herein can be used to monitor real-time or near real-time changes in the levels of specific follicular bulb biomarkers to determine exposure to toxicants. By utilizing the living, responsive cells in the plucked hair follicle bulb in an immunohistochemical (IHC) analysis, the various embodiments mitigate the risks of false positives associated with segmental hair analysis and avoid the more invasive collection required for serum and urinalysis. The various embodiments of the invention rely upon detection of various agent-responsive proteins (biomarkers) in intact, plucked hair follicle bulbs. Rather than measuring the toxicant or its metabolites, changes in specific toxicant-responsive follicle bulb proteins are monitored to determine toxicant exposure.

The invention further includes methods of varying scope.

DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

In the following detailed description of the present embodiments, reference is made to the accompanying drawings that form a part hereof, and in which is shown by way of illustration specific embodiments in which the invention may be practiced. These embodiments are described in sufficient detail to enable those skilled in the art to practice the invention, and it is to be understood that other embodiments may be utilized and that process, chemical or mechanical changes may be made without departing from the scope of the present invention. The following detailed description is, therefore, not to be taken in a limiting sense, and the scope of the present invention is defined only by the appended claims and equivalents thereof.

Carbamate, OP pesticides and OP nerve agents exert their effects through the inhibition of Acetylcholinesterase (AChE). Acetylcholinesterase is the enzyme responsible for the breakdown of the neurotransmitter acetylcholine (ACh). Following AChE inhibition, ACh accumulates in the synapses. As a result of the increased ACh concentration in the synapses, the portions of the sympathetic and parasympathetic nervous system that control smooth muscle, cardiac muscle and exocrine glandular function are overstimulated. Urine and blood tests are available to determine the presence of OP compound hydrolysis products. Although conclusive, most require derivatization prior to analysis. Currently, measurement of AChE levels in the blood is the fastest and most commonly employed method to determine exposure to pesticides and nerve agents. Although this test is faster than analyzing for hydrolysis products in the urine or blood, there are still several drawbacks to the test due to the inherent nature of AChE. First, it has been reported that there is a 10-18% interindividual variation and a 3 to 7% intraindividual variation for AChE levels. Thus, without a known personal baseline, it is difficult to conclude if a person has been exposed to a nerve agent if they show inhibition levels of less than 20%. Secondly, due to the de novo synthesis of new AChE, this method cannot be used for retrospective determination of exposure. The various embodiments of the invention facilitate simple and rapid determination of exposure to carbamate and OP pesticides and OP nerve agents.

In order to reduce the invasiveness of blood or urine based tests, a new methodology using plucked hair follicle bulbs was developed. Plucked hair follicle bulb collection is relatively non-invasive, can be performed in the field, and samples can be easily preserved, stored, and shipped. Additionally, enough hair samples can easily be collected and stored in order to repeat testing for further confirmation. By employing IHC, this method overcomes the false positives associated with traditional segmental hair analysis. By measuring the changes in specific biomarker levels in the living portion of the hair follicle bulb, the IHC technique employed in this method detects response to exposure in near real-time.

The concept of IHC began in the 1930s when several studies reported that antibodies could be "marked" with dye-groups and still retain their specific immunoreactivity. Several years later, it was demonstrated with labeled anti-typhoid serum and unlabeled anti-cholera serum that the color seen in the agglutinated typhoid was due to specific antibody binding and not non-specific absorption or occlusion of the dye in the cell. The immunofluorescence of mouse tissue infected with pneumococcus has been observed to occur in localized areas and the staining is immunologically specific. In the more than six decades since initial studies, many improvements have been made in IHC, allowing it to become a commonly employed laboratory technique.

IHC successfully bridges the fields of immunology, chemistry and histology, resulting in a simple, yet powerful research and diagnostic tool. Antibodies are used to identify specific antigens within tissue sections. Following antigen-antibody binding, the antigen is then demonstrated in the tissue with a colored dye or fluorochrome. Because intact tissue is used, IHC can be used to determine the location of specific antigens.

Disclosed herein are modifications to classical IHC methodologies in order to study intact, plucked rat whisker follicle bulbs. Unlike traditional segmental hair analysis in which the specific chemical or metabolites are extracted from the hair shaft and measured, the methods described herein can be used to monitor real-time or near real-time changes in the levels of specific follicular bulb biomarkers to determine exposure to toxicants. To date, seventeen OP nerve agent-responsive target proteins have been confirmed using Western Blotting and IHC. The methodology described herein may further find use in determining exposure to the OP nerve agent VX and the munitions compound Royal Demolition Explosive (RDX) as well as a variety of other toxicants.

By utilizing the living, responsive cells in the plucked hair follicle bulb in an IHC analysis, the various embodiments mitigate the risks of false positives associated with segmental hair analysis and avoid the more invasive collection required for serum and urinalysis. The various embodiments of the invention rely upon detection of various agent-responsive proteins (biomarkers) in intact, plucked hair follicle bulbs using a novel immunohistochemistry (IHC) method. Rather than measuring the toxicant or its metabolites, changes in specific toxicant responsive follicle bulb proteins are monitored to determine toxicant exposure. Seventeen potential biomarkers were identified for investigation. Table 1 lists these biomarkers. Multiple biomarkers were verified for use with embodiments of the invention.

TABLE I

Biomarker Candidates in the Rat Whisker Follicle Bulb

| Potential Biomarker | Function | Literature evidence (tissue type) |
| --- | --- | --- |
| Actin | Cytoskeletal; cell division | Rats exposed to sublethal dose of soman reported to have decreased levels of protein synthesis (brain) |
| Aldehyde Dehydrogenase (ALDH) | Metabolism; Phase II | Cells exposed to methylcholanthrene showed induction of ALDH (cell culture) |
| Androgen Receptor | Hormone Receptor | OP and OC pesticides were shown to act as antagonists of the AR |

TABLE I-continued

Biomarker Candidates in the Rat Whisker Follicle Bulb

| Potential Biomarker | Function | Literature evidence (tissue type) |
| --- | --- | --- |
| Brain derived neurotrophic factor (BDNF) | Neurotrophin | BDNF mRNA down-regulated in animals exposed to OP pesticides |
| CD 3 | Lymphocytes (T-lymphocytes) | Mice exposed to low-level sarin showed slight decreases of CD 3 (lungs) |
| CD 20 | Lymphocytes (B-lymphocytes) | Mice exposed to low-level sarin showed slight increases of CD 19 (lungs) |
| Cytochrome P450 1A1 (CYP 1A1) | Metabolism; Phase 1 | Cells exposed to β-naphthaoflavone, phenobarbital and methylcholanthrene showed increase CYP1A1 activity (cell culture) |
| Estrogen Receptor α | Hormone Receptor | OP pesticide diazinon demonstrated estrogenic activity in ovarian carcinoma cells (cell culture) |
| Glial cell line-derived neurotrophic factor (GDNF) | Neurotrophic factor; cytokine family | GDNF mRNA expression increased in rats exposed to sub-chronic doses of phencyclidine (rat brain); also known to aid in repair following neuronal damage |
| Glucose Transporter 1 | Membrane bound; transport | Cells exposed to lipophilic pesticides showed a decrease in glucose transporter activity (cell culture) |
| Glutathion-S-Transferase (GST) | Metabolism; Phase II | Cells exposed to methylcholanthrene showed induction of GST (cell culture) |
| NAD(P)H: Quinone Oxidoreductase I (NQO I) | Metabolism; Phase II | Cells exposed to methylcholanthrene showed induction of NQO I (cell culture) |
| Sodium-Potassium ATPase (α and β sub-units) | Membrane bound; ion transport | Cells exposed to lipophilic pesticides showed a decrease in Na+/K+-ATPase activity (cell culture) |
| α-Tubulin | Cytoskeletal; cell division | Rats exposed to sublethal doses of soman had decreased levels of protein synthesis (brain) |
| β-Tubulin | Cytoskeletal; cell division | Rats exposed to sublethal doses of soman had decreased levels of protein synthesis (brain) |
| Tumor Necrosis Factor-α (TNF-α) | Cytokine | Rats exposed to low-level sarin shown increased mRNA for TNF-α (brain) |

Hair follicles cycle through three stages: growth (anagen), involution (catagen) and rest (telogen). A number of proteins cycle along with the hair follicle growth stages, thus the growth stage of individual hairs can be monitored by the presence or absence of these specific cycling proteins. Correct measurement of growth stage is extremely important for research involving hair follicles. Hair follicle bulbs must be in the same growth stage in order to compare levels of proteins that change in response to agent exposure. Two control proteins are Alkaline phosphatase (AP) and Matrix Metalloproteinase-2 (MMP-2).

Alkaline Phosphatase (EC 3.1.3.1) (AP) is a zinc metalloenzyme with a wide range of cellular functions. There are four distinct forms of AP: Intestinal (IAP), Placental (PLAP), Placental-like (ALP-1) and Tissue Non-Specific (TNAP). The Tissue Non-Specific isoform of Alkaline Phosphatase was chosen for this work due to the fact that it is widely expressed in a number of tissues compared to the Intestinal, Placental and Placental-like isoforms, which are tissue specific. Since the 1940s, scientists have been studying the role of AP in hair growth. Increased interest in the role of AP in the hair follicle occurred when dermopathologists observed decreased or absent AP activity in early alopecia areata, an autoimmune response causing hair loss in patches.

The levels of AP have been studied in the Long-Evans hooded rat skin model. Slight levels of activity have been observed in early anagen. However, a marked increase has been observed in AP activity in late anagen, when rapid epithelial proliferation occurs. When the hair follicle is in telogen, AP activity is not observed. It has further been reported that human hair follicles show an absence of AP in the dermal papilla of telogen follicles. AP activity has been observed in all stages of hair growth in C57 BL-6 mouse skin. However, this data conflicts with the previous reports described above and there has been speculation that the observed differences might be due to strain specific differences.

Due to the conflicting reports on the presence of AP in the hair follicle only during growth stages, an additional growth control was used. Matrix Metalloproteinase-2 (EC 3.4.24.24) has been shown to play a key role in the remodeling and cell migration in the extracellular matrix. Growth stage dependent expression of MMP-2 mRNA has been studied in anterior dorsal skin of female Sprague-Dawley rats. Matrix Metalloproteinase-2 mRNA was strongly expressed in anagen hair follicles and weakly expressed in telogen follicles. Using the two growth control antibodies simultaneously, the growth stage of individual hair follicles can be determined with good confidence.

Most published reports using IHC to study the proteins in the hair follicle use sectioned skin biopsies. One manuscript was found to describe the use of unsectioned, plucked hair follicles in IHC, i.e., the study of DOPA-negative melanocytes. See, Horikawa, T. et al., DOPA-Negative Melanocytes in the Outer Root Sheath of Human Hair Follicles Express Premelanosomal Antigens But Not a Melanosomal Antigen or the Melanosome-Associated Glycoproteins Tyrosinase, TRP-1, and TRP-2. *The Journal of Investigative Dermatology* 1996, 106 (1), 28-35. Since the proteins of interest examined in this work are not found in the Outer Root Sheath (ORS), the methods of the various embodiments necessarily differ from the method described by Horikowa et al. By digesting the ORS, the internal structure of the hair follicle bulb can be examined without time-consuming sectioning.

Collection of Rat Whiskers

Whiskers of male and female Sprague-Dawley rats (Charles River Laboratories, Wilmington, Mass., USA) were pulled manually, with care to remove intact whisker bulbs and immediately snap frozen in liquid nitrogen and stored at −135° C. until analysis.

Antibodies

The mouse monoclonal antibodies used in this work were: anti-Actin (Novus Biologicals, Littleton, Colo., USA), anti-Breast Cancer Antigen 1 (BRCA 1) (Santa Cruz Biotechnology, Santa Cruz, Calif., USA), anti-CD3 (Santa Cruz Biotechnology, Santa Cruz, Calif., USA), anti-Glial cell-line derived neurotrophic factor (GDNF) (Santa Cruz Biotechnology, Santa Cruz, Calif., USA), anti-Glutathion S-Transferase (GST) (Chemicon, Temecula, Calif., USA), anti-Keratin 10 (Neo Markers, Fremont, Calif., USA), anti-Na$^+$/K$^+$ATPase α1 (Santa Cruz Biotechnology, Santa Cruz, Calif., USA), and anti-Na$^+$/K$^+$ATPase β1 (Santa Cruz Biotechnology, Santa Cruz, Calif., USA).

The rabbit polyclonal antibodies used in this work were: anti-Androgen Receptor (AR) (Santa Cruz Biotechnology, Santa Cruz, Calif., USA), anti-Brain Derived Neutrophic Factor (BDNF) (Santa Cruz Biotechnology, Santa Cruz, Calif., USA), anti-Cytochrome P450 1A1 (CYP1A1) (Santa Cruz Biotechnology, Santa Cruz, Calif., USA), anti-CD20 (Santa Cruz Biotechnology, Santa Cruz, Calif., USA), anti-Estrogen Receptor α (ER α) (Santa Cruz Biotechnology, Santa Cruz, Calif., USA), anti-Glyceraldehyde Phosphate Dehydrogenase (GAPDH) (Novus Biologicals, Littleton, Colo., USA), anti-Glucose Transporter 1 (Glut 1) (Santa Cruz Biotechnology, Santa Cruz, Calif., USA) and anti-NAD(P)H: quinone oxidoreductase 1 (NQO 1) (Santa Cruz Biotechnology, Santa Cruz, Calif., USA).

The goat polyclonal antibodies used in this work were: anti-Aldehyde Dehydrogenase 1A2 (ALDH1A2) (Santa Cruz Biotechnology, Santa Cruz, Calif., USA), anti-Tissue Non-Specific Alkaline Phosphatase (TNAP) (Santa Cruz Biotechnology, Santa Cruz, Calif., USA) and anti-Tumor Necrosis Factor-α (TNF-α) (Santa Cruz Biotechnology, Santa Cruz, Calif., USA).

The chicken polyclonal antibody used in this work was: anti-Matrix Metalloproteinase-2 (MMP-2) (Abcam, Cambridge, Mass., USA).

The Cy5-labeled goat anti-rabbit IgG and Cy5-labeled goat anti-mouse IgG were purchased from Amersham Biosciences (Pisataway, N.J., USA). Cy5-labeled and Cy3-labeled rabbit anti-goat IgG was purchased from Chemicon (Temecula, Calif., USA). Alexa Fluor 532-labeled anti-Chicken IgY was made from rabbit anti-Chicken IgY (Abcam, Cambridge, Mass., USA) labelled with the Alexa Fluor 532 Protein Labeling Kit (Molecular Probes, Eugene, Oreg., USA). Alkaline phosphatase conjugated anti-rabbit IgG, anti-mouse IgG, anti-goat IgG and anti-chicken IgY were purchased from Santa Cruz Biotechnology (Santa Cruz, Calif., USA).

SDS-PAGE and Western Blotting of Hair Protein

Protein was extracted from the bulb region of 15 to 25 hairs from donor rats. The hairs were cut to separate the bulb and shaft regions. The bulb region was then incubated in buffer as described by Inoue et al. at 37° C. for 96 hr. See, Inoue, T.; Kizawa, K.; Ito, M., Characterization of Soluble Protein Extracts from Keratinized Tissues: Identification of Ubiquitin Universally Distributed in Hair, Nail, and Stratum Corneum, *Bioscience, Biotechnology and Biochemistry* 2001, 65(4), 895-900. Following extraction, the proteins were dialyzed against 0.2 M Tris-HCl, pH 8.0 containing Complete Protease Inhibitor Cocktail tablets (Roche, Indianapolis, Ind., USA) at room temperature for 4 hr (2 buffer changes) and then at 4° C. overnight. Protein concentration was determined using the DC Protein Assay kit (BioRad, Hercules, Calif., USA). Extracts were separated by SDS-PAGE (Sodium Dodecyl Sulfate Polyacrylamide Gel Electrophoresis) using a 10-20% Tris-HCl Ready Gel (BioRad, Hercules, Calif., USA). Equal amounts of the hair protein extract were heated in an equal volume of 2× Sample Buffer (62.5 mM Tris-HCl, pH 6.8 containing 2% SDS, 20% Glycerol, and 0.01% Bromophenol Blue) at the temperature and time indicated in Table 2 for biomarker candidates and controls. Kaleidoscope size markers (BioRad, Hercules, Calif., USA) were run concurrently in each gel.

TABLE 2

Heating Conditions and Antibody Concentrations for Western Blot and IHC

| Potential Protein Biomarker | Heating Time (Temperature) | Primary Antibody Raised In | Concentration of Primary in Western Blot | Concentration of Secondary in Western Blot | Concentration of Primary in IHC |
|---|---|---|---|---|---|
| Actin | 3 min (100° C.) | Mouse | 1:75 | 1:5000 | 1:25 |
| ALDH 1A2 | 30 min (65° C.) | Goat | 1:30 | 1:28000 | 1:25 |
| AR | 3 min (100° C.) | Rabbit | 1:25 | 1:12000 | 1:25 |
| BDNF | 3 min (100° C.) | Rabbit | 1:25 | 1:18000 | 1:25 |
| BRCA 1 | 3 min (100° C.) | Mouse | 1:125 | 1:10000 | 1:25 |
| CD 3 | 10 min (95° C.) | Mouse | 1:30 | 1:20000 | N/A |
| CD 20 | 3 min (100° C.) | Rabbit | 1:75 | 1:16000 | 1:25 |
| CYP 1A1 | 3 min (100° C.) | Rabbit | 1:100 | 1:6000 | 1:25 |
| ER α | 30 min (65° C.) | Rabbit | 1:20 | 1:28000 | 1:25 |
| GAPDH | 3 min (100° C.) | Rabbit | 1:150 | 1:6000 | 1:25 |
| GDNF | 3 min (100° C.) | Mouse | 1:25 | 1:2500 | 1:25 |
| Glut 1 | 3 min (100° C.) | Rabbit | 1:100 | 1:6000 | 1:25 |
| GST | 30 min (65 ° C.) | Mouse | 1:75 | 1:12000 | 1:25 |
| Keratin 10 | 3 min (100° C.) | Mouse | 1:100 | 1:2000 | 1:25 |
| MMP 2 | 30 min (65° C.) | Chicken | 1:500 | 1:15000 | 1:50 |
| NQO 1 | 30 min (65° C.) | Rabbit | 1:30 | 1:28000 | 1:25 |
| Na$^+$/K$^+$-ATPase α1 | 30 min (65° C.) | Mouse | 1:20 | 1:12000 | N/A |
| Na$^+$/K$^+$-ATPase β1 | 3 min (100° C.) | Mouse | 1:25 | 1:2500 | 1:25 |

TABLE 2-continued

Heating Conditions and Antibody Concentrations for Western Blot and IHC

| Potential Protein Biomarker | Heating Time (Temperature) | Primary Antibody Raised In | Concentration of Primary in Western Blot | Concentration of Secondary in Western Blot | Concentration of Primary in IHC |
|---|---|---|---|---|---|
| TNF-α | 30 min (65° C.) | Goat | 1:30 | 1:28000 | 1:25 |
| TNAP | 10 min (95° C.) | Goat | 1:20 | 1:23000 | 1:25 |
| α-Tubulin | 3 min (100° C.) | Mouse | 1:100 | 1:3000 | 1:25 |
| β-Tubulin | 30 min (65 ° C.) | Mouse | 1:50 | 1:12000 | 1:25 |

Following electrophoresis, the gel was incubated for 15 min in Transfer Buffer (25 mM $K_2HPO_4$, 25 mM $KH_2PO_4$, and 0.25 mM EDTA). The proteins were then transferred onto 0.45 μm nitrocellulose membranes (Schleicher and Schuell, Keene, N.H., USA) in a BioRad Mini Protean Transfer Cell (BioRad, Hercules, Calif., USA).

Following transfer, the nitrocellulose membranes were incubated with Antibody Extender Solution (Pierce, Rockford, Ill., USA) at room temperature for 10 min. The nitrocellulose membranes were blocked in TTBS (50 mM Tris, pH 8.0 containing 150 mM NaCl and 0.5% Tween) containing 5% BSA overnight 4° C. Primary antibodies were diluted to a concentration of between 1:20 and 1:50 in TTBS containing 5% BSA (see Table 2 for dilutions). The membranes were incubated with the primary antibody at 37° C. for 4 hr. The membranes were washed with TTBS 4 times, 5 min per wash. Dye-conjugated secondary antibodies were diluted in TTBS containing 5% BSA (see Table 2 for dilutions). The membranes were incubated in secondary antibody at room temperature for 1 hr. Following removal from secondary antibody, the membranes were washed in TTBS 4 times, 5 min per wash, and rinsed in $diH_2O$ 3 times, 2 min per rinse. Membranes were developed with NBT/BCIP (Roche, Indianapolis, Ind., USA) at room temperature until sufficient color development occurred.

Immunohistochemistry

Hair samples were fixed briefly in fresh acetone, removed and incubated in TBS (50 mM Tris, pH 8.0 containing 150 mM NaCl) at room temperature for 15 minutes. The hairs were mounted onto glass slides, leaving the bulb and lower shaft of the follicle free and digested with 0.1 mg/ml Proteinase K (Invitrogen, Carlsbad, Calif., USA) in 20 mM Tris-HCl, pH 7.5 containing 50 mM $CaCl_2$ at 37° C. for 1 hr. Following digestion, the entire slide was washed with TTBS 4 times, 5 min per wash. Individual hair follicle lower shaft and bulb were blocked at room temperature for 10 minutes with TTBS containing 5% BSA. The blocking solution was blotted off and each hair follicle lower shaft and bulb was covered with primary antibody (1:25-1:50) (see Table 2 for dilutions). Slides were incubated at 4° C. overnight in a humidity chamber. Following incubation with the primary antibody, slides were washed with TTBS 4 times, 5 min per wash. Each lower shaft and hair follicle bulb was immersed in Cy5-labeled secondary antibody (1:400). Slides were incubated at room temperature for 1 hr in darkness. Following secondary antibody incubation, slides were washed 4 times, 5 min per wash, with TTBS. For triple labeling, 10 μl of an anti-TNAP (1:25) and anti-MMP-2 (1:50) mixture was used to cover each hair follicle lower shaft and bulb. Slides were incubated in a dark humidity chamber at room temperature for 1 hr. Following incubation with the anti-TNAP/anti-MMP-2 mixture, the slides were washed with TTBS 4 times, 5 min per wash. Hairs were covered with a mixture Cy3-labeled rabbit anti-goat IgG (1:400) and Alexa 532 rabbit anti-chicken IgY (1:400) in a dark humidity chamber at room temperature for 1 hr. Slides were washed with TTBS 4 times, 5 min per wash, and rinsed with $diH_2O$ 3 times, 2 min per wash. Images were analyzed on Affymetrix 428 scanner (Affymetrix, Santa Clara, Calif., USA) using Affymetrix Jaguar 2.0 software (Affymerix, Santa Clara, Calif., USA).

Western Blot Confirmation

Figure 1:
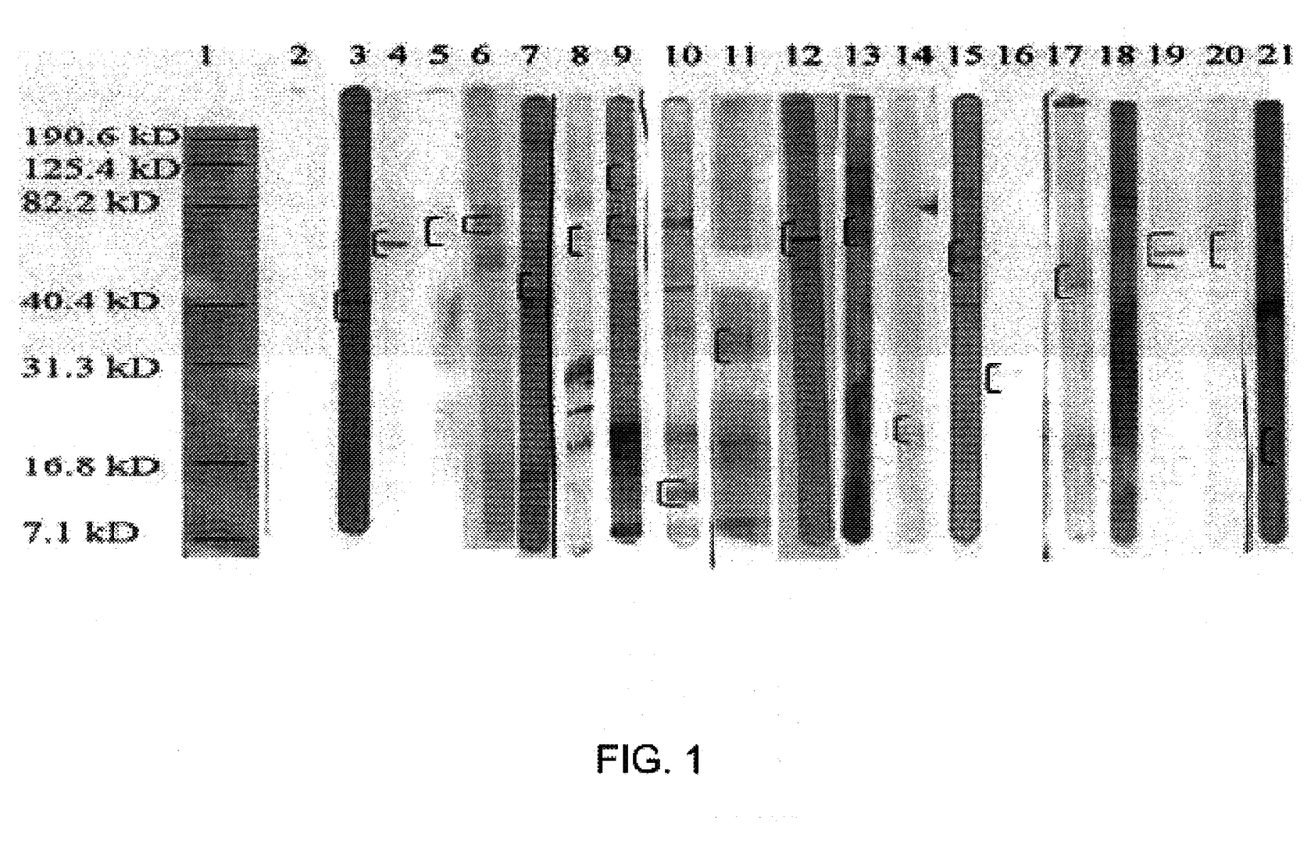
FIG. 1 shows Western blotting results of various biomarkers in accordance with an embodiment of the invention.

All targets chosen for study were due to their role in skin biology or OP pesticide or nerve agent response. Western Blots were performed to ensure that the specific protein of interest was located in the hair bulb. FIG. 1 shows Western blotting confirmation of all targets. Of the potential targets from Table 1, all could be verified in the bulb region of the follicle except CD3 and $Na^+/K^+$-ATPase α1. In FIG. 1, the figure shows the Western Blot of total rat follicle bulb protein separated by 10-20% SDS-PAGE. The lanes are: 1: BioRad Kaleidoscope Molecular Weight Ladder; 2: BRCA 1; 3: GAPDH; 4: Keratin 10; 5: MMP-2; 6: TNAP; 7: Actin; 8: ALDH 1A2; 9: AR; 10: BDNF; 11: CD 20; 12: CYP 1A1; 13: ER α; 14: GDNF; 15: GLUT 1; 16: GST; 17: $Na^+/K^+$-ATPase β1; 18: NQO I; 19: α-Tubulin; 20: β-Tubulin; and 21: TNF-α.

CD 3 is the designation given to the multi-subunit complex of proteins that associate with the T cell antigen receptor (TCR). It has been reported that only 5 cells out of 100 hair follicles express TCR in the distal outer root sheath, thus TCR is found extremely rarely in the hair follicle. The reported rarity of finding TCR in the hair follicle may explain why the Western blotting carried out in this work did not confirm CD 3 in the rat whisker hair follicle bulb.

The $Na^+/K^+$-ATPase α1 subunit was the other potential target that could not be confirmed by the Western Blotting in the experiments described herein. However, the Western blotting confirmed the β1 subunit of the $Na^+/K^+$-ATPase among follicle proteins. The α1 and β1 subunits are found in a 1:1 ratio in the plasma membrane complex $Na^+/K^+$-ATPase. The lack of confirmation of the α1 subunit may be due to the epitope of the antibody used or the fact that 32% of the α subunit protein mass is found in the lipid-associated membrane region. Only a small portion of the β-subunit protein mass is found in the lipid associated region, which could explain the confirmation of the β-subunit in the rat whisker follicle by Western blotting.

Proteinase K Timecourse

Proteinase K (EC 3.4.21.14) is a non-specific serine protease commonly used in IHC to digest tissue samples to retrieve epitopes and reduce background immunoreactivity. Termed Protease-Induced Epitope Retrieval (PIER), this technique has been described for the retrieval of keratins in cancerous tissue. See, Huang, S.; Minassian, H.; More, J. D., Application of Immunofluorescent Staining on Paraffin Sections Improved by Trypsin Digestion, *Laboratory Investigation* 1976, 35 (4), 383-390. In this technique, enzymes such as trypsin, proteinase K, pronase, ficin, and/or pepsin are used to non-specifically digest proteins in a fixed sample in order to retrieve epitopes of interest. However, care must be taken in order to ensure that epitopes are not destroyed by excessive enzyme digestion.

The PIER technique employed for this work was achieved by Proteinase K in order to digest the fibrous Outer Root Sheath (ORS) of the rat whisker follicle bulb. To optimize this technique for the investigation of the rat whisker bulb, a series of PIER time course experiments were carried out. The efficiency of the Proteinase K digestion was measured using anti-Keratin 10 and anti-MMP-2. Keratin 10, a positive control protein, is expressed in the epidermis and inner-root sheath (IRS) of normal human and dog hair. However, Keratin 10 is not expressed in the ORS. In order to control for the growth stage of the whisker, the protein MMP-2 was probed. However, unlike Keratin 10, it is expressed in the ORS and other layers within the hair bulb.

Figure 2A:
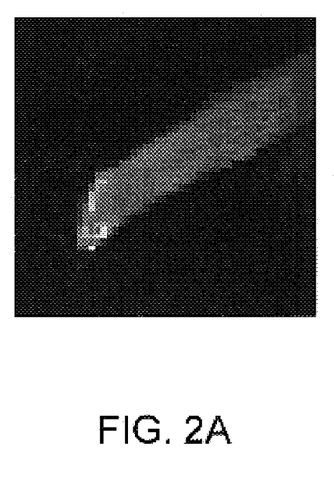
FIGS. 2A-2D depict Proteinase K digestion of rat whisker follicle bulbs at various stages in accordance with an embodiment of the invention.
Figure 2B:
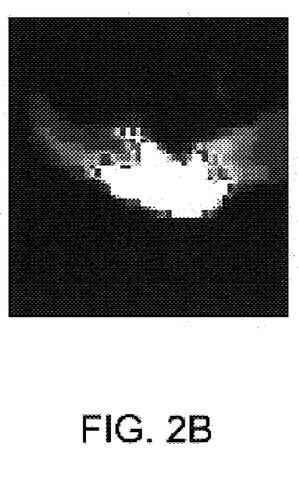
Figure 2C:
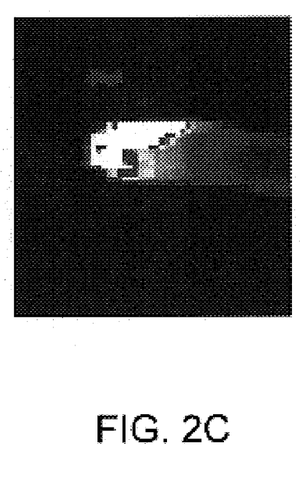
Figure 2D:
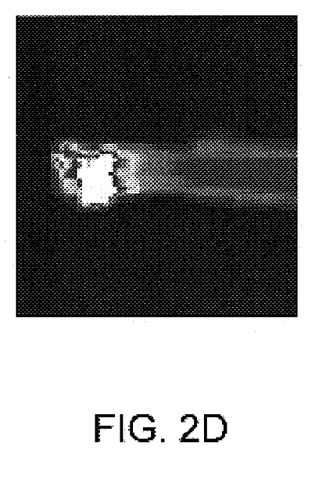

FIGS. 2A-2D depict Proteinase K digestion of rat whisker follicle bulbs at various stages. FIG. 2A shows an undigested whisker bulb, FIG. 2B shows a whisker bulb digested for 30 minutes with Proteinase K, FIG. 2C shows a whisker bulb digested for 60 minutes with Proteinase K, and FIG. 2D shows a whisker bulb digested for 90 minutes.

By using this growth stage indicator expressed in the ORS, the growth stage of the hair follicle bulb can be controlled for between whiskers used in the PIER procedure optimization. When the ORS is still intact, there should be no interactions of the Keratin 10 antibody with the specific protein. Only after the Proteinase K digests the ORS, should any interactions of Keratin 10 with the specific antibody be observed. Thus, the digestion timing can be optimized to expose the proteins found beneath the ORS.

As expected, there was minimal Keratin 10 immunoreactivity, but strong MMP-2 immunoreactivity before any proteinase K digestion (FIG. 2A). Following 30 and 60 minutes of digestion, the ORS was digested, as evidenced by the abundance of Keratin 10 antibody binding (FIGS. 2B and 2C). As the ORS was digested, MMP-2 was still clearly observed in the IRS. One of the dangers of PIER is the possibility of over-digestion, resulting in destruction of the epitope of interest. As shown in FIG. 2D, after 90 minutes of Proteinase K digestion, some of the Keratin 10 epitope has been destroyed. This is evidenced by the fact that the whisker is in an active state, however the areas of active growth are beginning to show diminished Keratin 10 immunoreactivity. Based on the data shown in FIGS. 2A-2D, a 60-minute digestion was determined optimal for these given PIER conditions; the ORS was digested, yet the epitopes containing the regions of interest were not damaged.

Intact Hair Follicle Bulb IHC

In order to further confirm the presence of potential targets in the hair bulb, IHC using antibodies for the specific target proteins was performed. All hair protein targets with positive results in Western blotting experiments were further verified in the intact hair follicle bulb using modified, whole mount IHC.

In order to ensure that observed immunoreactivity results were not due to non-specific binding of the secondary antibody, negative controls experiments were performed. The chicken, goat, and rabbit secondary antibodies used in the IHC all produce minimal background immunoreactivity. However, using a mouse secondary antibody results in slightly higher background levels. This increased background observed when using a mouse secondary antibody is likely the result of the significant protein homology between the rat and mouse. Based on these results, it was determined that polyclonal antibodies produced in chicken, goat, and rabbit are generally preferred.

An additional negative control antibody, anti-BRCA 1, was employed in these experiments. Since BRCA 1 proteins are not found in the hair follicle, no fluorescence should be observed. The total fluorescence for a hair bulb stained for BRCA 1 is negligible. The hair bulb probed with anti-BRCA 1 in this example appeared to have less background than the hair bulb probed with only the mouse secondary antibody. While both bulbs in this example were actively growing, analysis of the MMP-2 and TNAP immunoreactivity patterns revealed they are not in the same growth stage. If the bulb of the hair probed with anti-BRCA 1 was in the same growth stage as the mouse secondary antibody negative control, the background levels likely would have been similar.

As noted above, the whole mount immunohistochemistry methods of the various embodiments may be used to detect exposure to a variety of toxicants from a single intact hair. One example of a toxicant of interest is Hexahydro-1,3,5-trinitro-1,3,5-triazine, more commonly known as RDX (for Royal Demolition Explosive). RDX is a highly explosive nitroaromatic compound used in military munitions (Bhushan et al., 2003). RDX was widely used in World War II and comprises 91% of Composition C-4 plastic explosive. RDX is highly toxic to humans and animals, resulting in central nervous system related convulsions and hyperactivity of the liver, lung, and kidney. Unfortunately, unlike pesticides and other simple nitroaromatic compounds, explosives such as 2,4,6-trinitrotoluene (TNT), RDX and octahydro-1,3,5,7-tetranitro-1,2,5,7-tetrazine (HMX) are less biodegradable than pesticides and other simple nitroaromatic compounds and persist in the soil and water of contaminated sites.

To observe protein expression changes in rats exposed to RDX, male rats, approximately six weeks old, were exposed to either 3 mg/kg ("low" dose) or 18 mg/kg ("high" dose) of 99% pure RDX powder by gavage (pill by mouth). Three animals from each dosage group were euthanized 24 and 48 hours following exposure. At the time of death, whiskers were collected by pulling manually, snap freezing in liquid nitrogen and storing at −80° C. until use.

Hair samples were briefly fixed in fresh acetone, removed and incubated in TBS (Tris, pH 8.0) for 15 minutes at room temperature. Hairs were mounted onto glass slides, leaving the bulb and lower shaft of the follicle free. The hairs were digested with Proteinase K (Invitrogen, Carlsbad, Calif., USA) in 20 mM Tris-HCl, pH 7.5 containing 50 mM CaCl2 for 1 hour at 37° C. Following digestion, the entire slide was washed with TTBS 4 times, 5 minutes per wash. Individual hair follicle lower shaft and bulb were incubated with blocking solution (TTBS containing 5% BSA) at room temperature for 10 minutes. Following the removal of the blocking solution, each hair follicle bulb and lower shaft was then covered with primary antibody (1:25-1:50). Slides were incubated at 4° C. overnight in a humidity chamber. Following incubation with the primary antibody, slides were washed with TTBS 4 times. Then each lower shaft and hair follicle was immersed in Cy5-labeled secondary antibody (1:400). Slides were incubated at room temperature for 1 hour in darkness. Following secondary antibody incubation, slides were washed 4 times, 5 minutes per wash, with TTBS. For triple labeling, 10 µl of an anti-TNAP (1:25) and anti-MMP-2 (1:50) mixture were used to cover each hair follicle. Slides were then incubated in a humidity chamber at room temperature for 1 hour in darkness. Following incubation with anti-TNAP and anti-MMP 2, the slides were then washed with TTBS 4 times. Hairs were incubated in a mixture of Cy3 labeled rabbit anti-goat IgG (1:400) and Alexa Fluor 532 labeled rabbit anti-chicken IgY (1:400) for 1 hour at room temperature in a dark humidity chamber. Slides were again washed with TTBS 4 times and rinsed with ddiH20 3 times. Images were analyzed on an Affymetrix 428 scanner (Affymetrix, Santa Clara, Calif., USA) using Affymetrix Jaguar 2.0 software (Affymetrix, Santa Clara, Calif., USA). Table 3 lists protein expression changes to six potential biomarkers as noted following such preparation and analysis.

TABLE 3

IHC Results from Stage-Matched RDX Exposed Whiskers (Three Matched Whiskers per Target)

| Potential Biomarker | Timepoint (hrs) | Protein Expression Change |
|---|---|---|
| Andogen Receptor | 24 | Up |
|  | 48 | Up |
| CYP 1A1 | 24 | Up |
|  | 48 | No Change |
| Estrogen Receptor α | 24 | No Conclusion |
|  | 48 | Up |
| GDNF | 24 | Up |
|  | 48 | Up |
| GLUT 1 | 24 | Down |
|  | 48 | No Change |
| GST | 24 | Down |
|  | 48 | Down |

Figure 3:
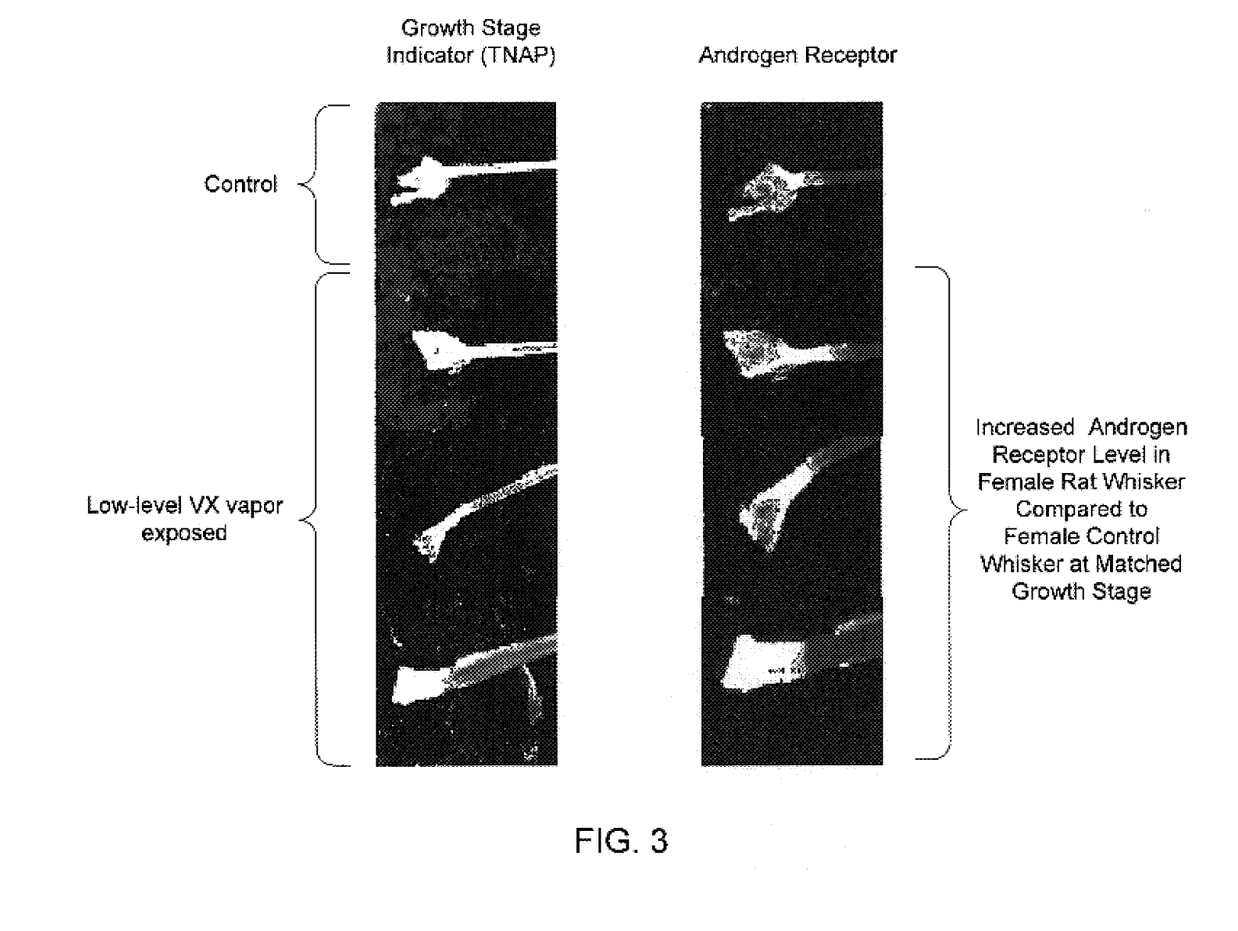
FIG. 3 depicts changes in Androgen Receptor expression following low-level VX vapor exposure in accordance with an embodiment of the invention.

FIG. 3 depicts changes in Androgen Receptor expression following low level VX Vapor Exposure. The exposure level was approximately 0.00067 mg/m$^3$ for 240 minutes. Female rats exposed to VX vapor at levels causing miosis in 10% of the animals (ECT10) show increased expression of Androgen Receptor.

Figure 4:
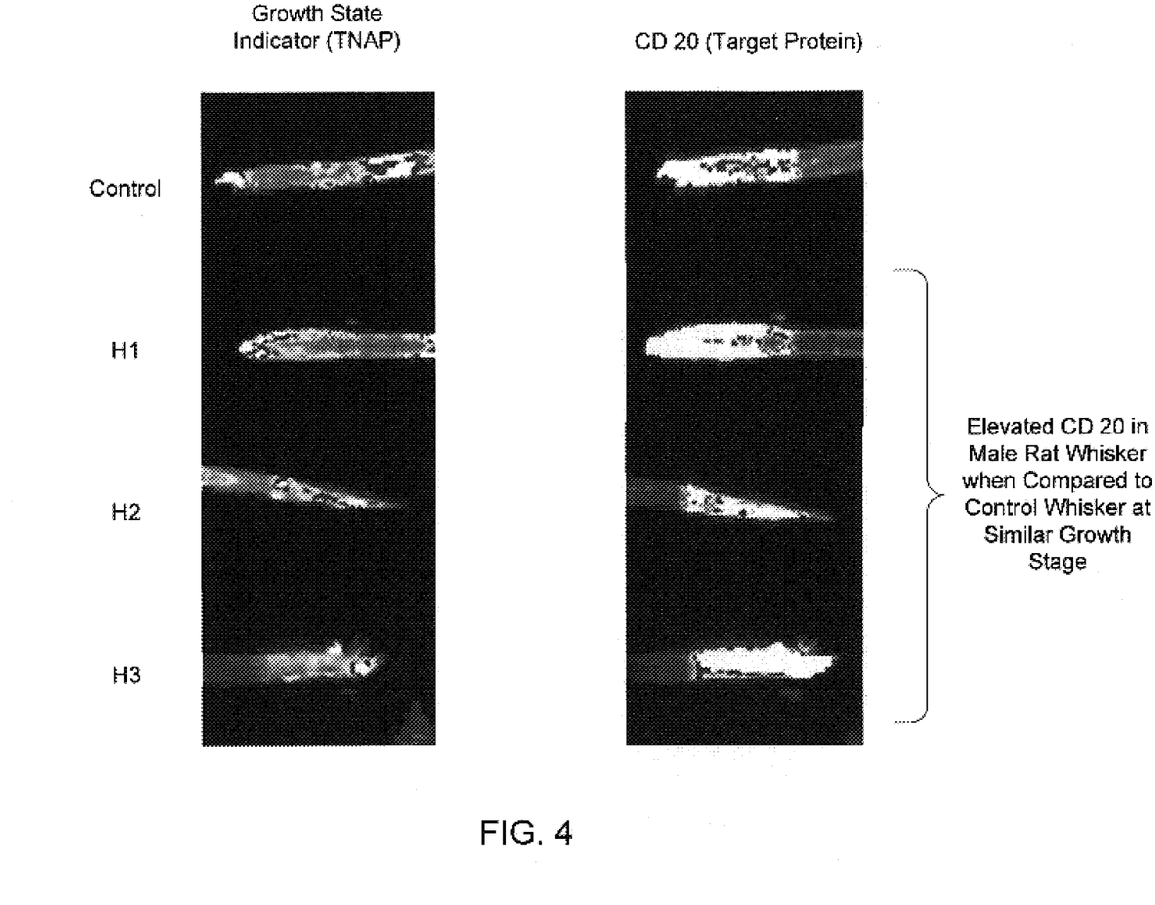
FIG. 4 depicts changes in CD20 level following RDX exposure in accordance with an embodiment of the invention.
Figure 5:
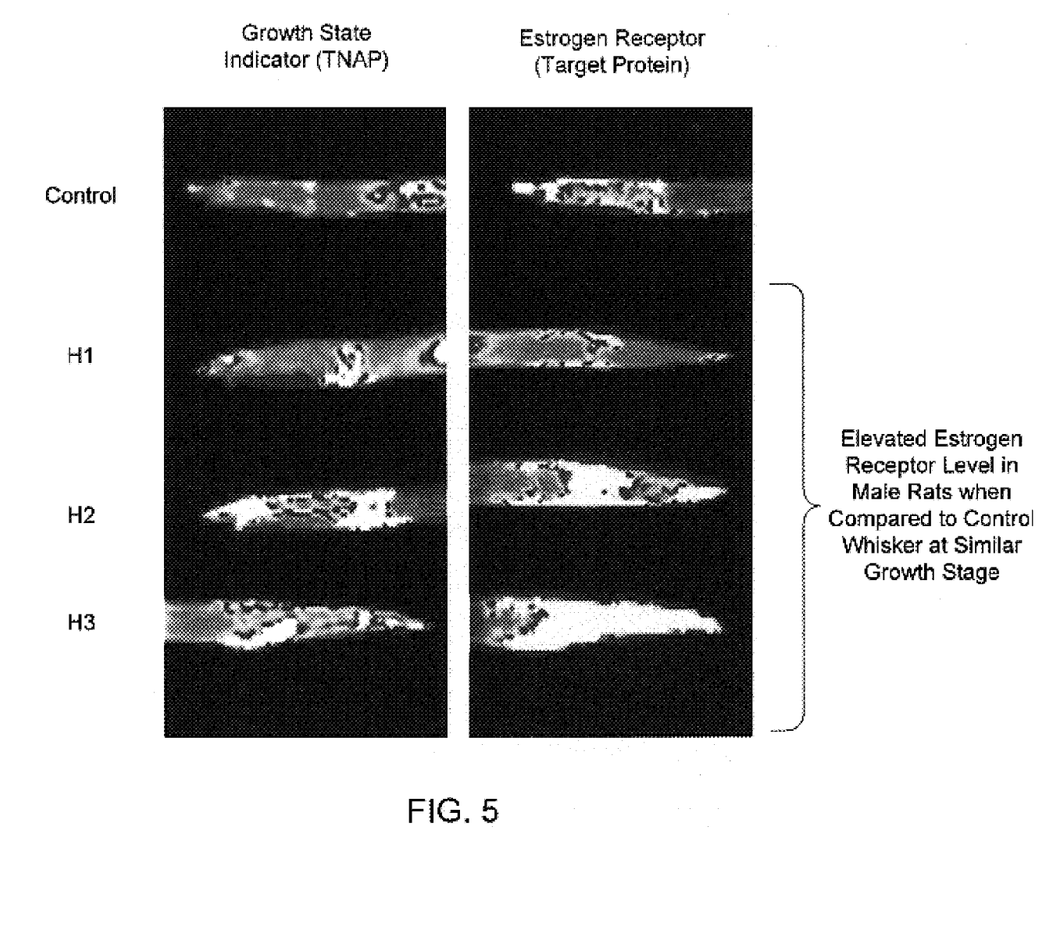
FIG. 5 depicts changes in Estrogen Receptor α level expression following RDX exposure in accordance with an embodiment of the invention.

FIG. 4 depicts changes in CD20 level expression following exposure to RDX. These males rats were exposed by gavage and killed at 24 hours and 48 hours after exposure was initiated. Whiskers were plucked immediately after death, and snap frozen and stored in liquid nitrogen prior to preparation. H1-H3 of FIG. 4 represent biological triplicates of 48 hours post 18 mg/kg RDX gavage. Similarly, FIG. 5 depicts changes in Estrogen Receptor α level expression following the same levels of RDX exposure. H1-H3 of FIG. 5 represent biological triplicates of 48 hours post 18 mg/kg RDX gavage.

CONCLUSION

Detection of chemical exposure through the preparation of intact, plucked hair follicle bulbs has been described herein. The methods described herein can be used to monitor real-time or near real-time changes in the levels of specific follicular bulb biomarkers to determine exposure to toxicants. By utilizing the living, responsive cells in the plucked hair follicle bulb in an immunohistochemical (IHC) analysis, the various embodiments mitigate the risks of false positives associated with segmental hair analysis and avoid the more invasive collection required for serum and urinalysis. The various embodiments of the invention rely upon detection of various agent-responsive proteins (biomarkers) in intact, plucked hair follicle bulbs. Rather than measuring the toxicant or its metabolites, changes in specific toxicant-responsive follicle bulb proteins are monitored to determine toxicant exposure.

Although specific embodiments have been illustrated and described herein, it will be appreciated by those of ordinary skill in the art that any arrangement that is calculated to achieve the same purpose may be substituted for the specific embodiments shown. Many adaptations of the invention will be apparent to those of ordinary skill in the art. Accordingly, this application is intended to cover any adaptations or variations of the invention. It is manifestly intended that this invention be limited only by the following claims and equivalents thereof.

What is claimed is:

1. A method of detecting exposure of a subject to a chemical agent, comprising:
   collecting a hair sample from said subject;
   digesting an outer root sheath of a hair follicle bulb from said hair sample;
   binding antigens with antibodies after digesting said outer root sheath of said hair follicle, wherein at least one antibody binds antigens indicative of a growth stage of the hair follicle bulb in order to determine that the hair follicle bulb is in the anagen growth stage, and at least one other antibody binds antigens comprising chemical agent-responsive proteins;
   staining, by immunoreagents, layers of the hair follicle bulb, wherein the immunoreagents provide an indication of the bound antigen comprising said chemical agent-responsive proteins in the hair follicle bulb; and
   detecting a change in level of the chemical agent-responsive proteins from the stained hair follicle bulb for hair follicle bulbs in the anagen growth stage as an indication of exposure of the subject to the chemical agent, wherein said change in level is determined by comparing the level found in the subject to that of a control.

2. The method of claim 1, wherein digesting the outer root sheath comprises digesting with Proteinase K.

3. The method of claim 1, wherein the at least one antibody that binds antigens indicative of a growth stage of the hair follicle bulb is selected from the group consisting of anti-Tissue Non-Specific Alkaline Phosphatase and anti-Matrix Metalloproteinase-2.

4. The method of claim 1, wherein the chemical agent-responsive proteins include at least one protein selected from the group consisting of Actin, Aldehyde Dehydrogenase, Androgen Receptor, Brain-derived neurotrophic factor, CD 20, Cytochrome P450 1A1, Estrogen Receptor α, Glial cell line-derived neurotrophic factor, Glucose Transporter 1, Glutathion-S-Transferase, NAD(P)H: Quinone Oxidoreductase I, Sodium-Potassium ATPase β1, α-Tubulin, β-Tubulin, and Tumor Necrosis Factor-α.

5. The method of claim 1, wherein the immunoreagents are selected from the group consisting of dye-labeled or fluorochrome-labeled immunoglobulins.

6. The method of claim 5, wherein the dye-labeled or fluorochrome-labeled immunoglobulins are selected from the group consisting of Cy5-labeled goat anti-rabbit IgG, Cy5-labeled goat anti-mouse IgG, Cy5-labeled rabbit anti-goat IgG, Cy3-labeled rabbit anti-goat IgG, and Alexa Fluor 532-labeled anti-Chicken IgY.

7. The method of claim 1, wherein the chemical agent is selected from the group consisting of Carbamate, Organophosphate (OP) pesticides, Organophosphate (OP) nerve agents, 0-ethyl S-(2-diisopropylamino)ethyl methylphosphonothiolate (VX), Hexahydro-1,3,5-trinitro-1,3,5-triazine (RDX), and Octahydro-1,3,5,7-tetranitro-1,2,5,7-tetrazine (HMX).

8. The method of claim 7, wherein the chemical agent is RDX and the chemical agent-responsive proteins are selected from the group consisting of Androgen Receptor, Cytochrome P450 1A1, Estrogen Receptor α, Glial cell line-derived neurotrophic factor, Glucose Transporter 1, and Glutathion-S-Transferase.

* * * * *